(12) United States Patent
Ghouri

(10) Patent No.: US 9,396,308 B1
(45) Date of Patent: Jul. 19, 2016

(54) PHYSIOLOGICAL IMAGERY GENERATOR SYSTEM AND METHOD

(75) Inventor: Ahmed Ghouri, San Diego, CA (US)

(73) Assignee: HUMANA INC., Louisville, KY (US)

( * ) Notice: Subject to any disclaimer, the term of this patent is extended or adjusted under 35 U.S.C. 154(b) by 499 days.

(21) Appl. No.: 12/765,640

(22) Filed: Apr. 22, 2010

Related U.S. Application Data

(60) Provisional application No. 61/171,628, filed on Apr. 22, 2009.

(51) Int. Cl.
*A61B 5/00* (2006.01)
*G06F 19/00* (2011.01)
*G06F 17/10* (2006.01)
*G06F 17/00* (2006.01)

(52) U.S. Cl.
CPC . *G06F 19/34* (2013.01); *A61B 5/72* (2013.01); *A61B 5/74* (2013.01); *A61B 5/742* (2013.01); *G06F 17/10* (2013.01); *G06F 19/3406* (2013.01); *G06F 19/3431* (2013.01); *G06F 19/3437* (2013.01); *G06F 19/3487* (2013.01)

(58) Field of Classification Search
CPC .......... A61B 5/74–5/745; G06F 19/30–19/366
See application file for complete search history.

(56) References Cited

U.S. PATENT DOCUMENTS

| | | | |
|---|---|---|---|
| 6,032,119 A * | 2/2000 | Brown et al. .................. 705/2 |
| 6,584,445 B2 * | 6/2003 | Papageorge .................. 705/3 |
| 6,692,258 B1 * | 2/2004 | Kurzweil et al. ............. 434/262 |
| 7,120,298 B1 * | 10/2006 | Staehle ......................... 382/166 |
| 8,032,394 B1 * | 10/2011 | Ghouri ............................. 705/2 |
| 2002/0107705 A1 * | 8/2002 | Boucher ......................... 705/2 |
| 2003/0018245 A1 * | 1/2003 | Kaufman et al. ............ 600/407 |
| 2004/0122787 A1 * | 6/2004 | Avinash et al. ................ 706/50 |
| 2006/0085223 A1 * | 4/2006 | Anderson et al. ............... 705/2 |
| 2006/0089543 A1 * | 4/2006 | Kim et al. ..................... 600/300 |
| 2007/0088525 A1 * | 4/2007 | Fotiades et al. .............. 702/131 |
| 2007/0106535 A1 * | 5/2007 | Matsunaga ...................... 705/3 |
| 2007/0118399 A1 * | 5/2007 | Avinash et al. .................. 705/2 |
| 2008/0015893 A1 * | 1/2008 | Miller et al. ..................... 705/2 |
| 2008/0015894 A1 * | 1/2008 | Miller et al. ..................... 705/2 |
| 2008/0077019 A1 * | 3/2008 | Xiao et al. .................... 600/474 |
| 2008/0088629 A1 * | 4/2008 | Lorenz et al. .............. 345/440.2 |
| 2008/0097784 A1 * | 4/2008 | Miller et al. ..................... 705/2 |
| 2008/0126117 A1 * | 5/2008 | Miller et al. ..................... 705/2 |
| 2008/0130968 A1 * | 6/2008 | Daw et al. ..................... 382/128 |
| 2008/0235049 A1 * | 9/2008 | Morita et al. .................... 705/2 |
| 2008/0253628 A1 * | 10/2008 | Matsue et al. ................ 382/128 |
| 2008/0306353 A1 * | 12/2008 | Douglas et al. .............. 600/301 |
| 2009/0054755 A1 * | 2/2009 | Shiibashi ...................... 600/407 |
| 2009/0192821 A9 * | 7/2009 | Park et al. ......................... 705/3 |
| 2009/0264814 A1 * | 10/2009 | Krijnsen et al. ................ 604/66 |
| 2009/0299767 A1 * | 12/2009 | Michon et al. .................. 705/3 |
| 2009/0315259 A1 * | 12/2009 | Riley ............................ 273/242 |
| 2010/0010827 A1 * | 1/2010 | Fueyo et al. ..................... 705/2 |
| 2010/0049547 A1 * | 2/2010 | Mirza et al. ...................... 705/3 |
| 2010/0092055 A1 * | 4/2010 | Matsuda ........................ 382/128 |
| 2011/0298806 A1 * | 12/2011 | Rasmussen .................. 345/440 |

* cited by examiner

*Primary Examiner* — William Thomson
*Assistant Examiner* — Marie Archer
(74) *Attorney, Agent, or Firm* — Standley Law Group LLP

(57) ABSTRACT

A system and method that generates a physiological imagery of one or more parts of a patient's body are provided. The system and method combine one or more parameters relating to a particular part of the body and then generates the physiological imagery for the part of the body wherein the physiological imagery may have a characteristic that changes based on the state of the patient.

25 Claims, 4 Drawing Sheets

PHYSIOLOGICAL IMAGERY GENERATOR SYSTEM AND METHOD

PRIORITY CLAIMS/RELATED APPLICATIONS

This application claims the benefit under 35 USC 119(e) and the priority under 35 USC 120 to U.S. Provisional Patent Application Ser. No. 61/171,628 filed on Apr. 22, 2009 and entitled "Physiological Imagery Generator System and Method", the entirety of which is incorporated by reference herein.

FIELD

The disclosure relates generally to medical visualization and in particular to a system and method that generates imagery for a state of the patient so that the state of the patient can be rapidly visualized.

BACKGROUND

Physicians are besieged with information overload and a lack of time to see patients. For example, a typical US office-based doctor can spend 7-10 minutes on average per patient, and may see 30 patients per day. In critical settings, such as the ICU, there may be more time spent per patient, but there is a flood of information from multiple sensors, monitors, and ventilators, for example, and often decisions of life-or-death importance must be made within minutes to seconds.

Today's electronic medical records systems present raw information to the doctor, such as a list of individual diagnoses, a list of current medications, and a list of individual lab results. This is wholly insufficient for time-pressed physicians who must read and interpret each individual data point into a mental picture of the state of the patient. This process is fraught with error and is humanly unscalable as the volume of information available for a patient grows without bound. Numbers and words grow exponentially without the ability to cross-correlate or interpret them in a simple, visualizable way that fosters insight into decision making.

Systems exist that provide an anatomical avatar that shows a body part and may have pieces of medical data, such as X-rays, etc. associated with the body part that a doctor/user can access. However, these anatomical avatar systems do not interpret the pieces of medical data nor provide a visual way to assess the state of the patient or the state of a body part/organ system of the patient.

Thus, it is desirable to provide a physiological imagery generating system and method by providing a visualization of the physiology, and it is to this end that the system and method are directed.

DETAILED DESCRIPTION OF ONE OR MORE EMBODIMENTS

The system and method are particularly applicable to a web-based system and it is in this context that the system and method will be described. It will be appreciated, however, that the system and method has greater utility because: 1) the system and method can be implemented in various manners that are within the scope of the system so that the system and method are not limited to the example web-based system described below; and 2) the system and method can be used to generate various different types of physiological imagery and the system and method are not limited to the examples provided below.

The system and method abstracts all medical data points/medical parameters for a patient into visualizable physiologic parameters that are independent of any single data point, and represent the synthesis of multiple related data points into a coherent interpretation of physiology and derangement due to disease. Additionally, the synthesis is performed in real-time, so that the arrival of any single data point can change the entire visualization schema without any human intervention, research, or request. For example, arrival of a profoundly elevated liver function test which infers injury to the bile duct can change the entire interpretation of the function of the organ (in this case, the exocrine function of the liver). Moreover, the physiologic image can be decomposed into reasoned elements so that the doctor can understand the basis for the imagery in an intuitive fashion.

Figure 1:
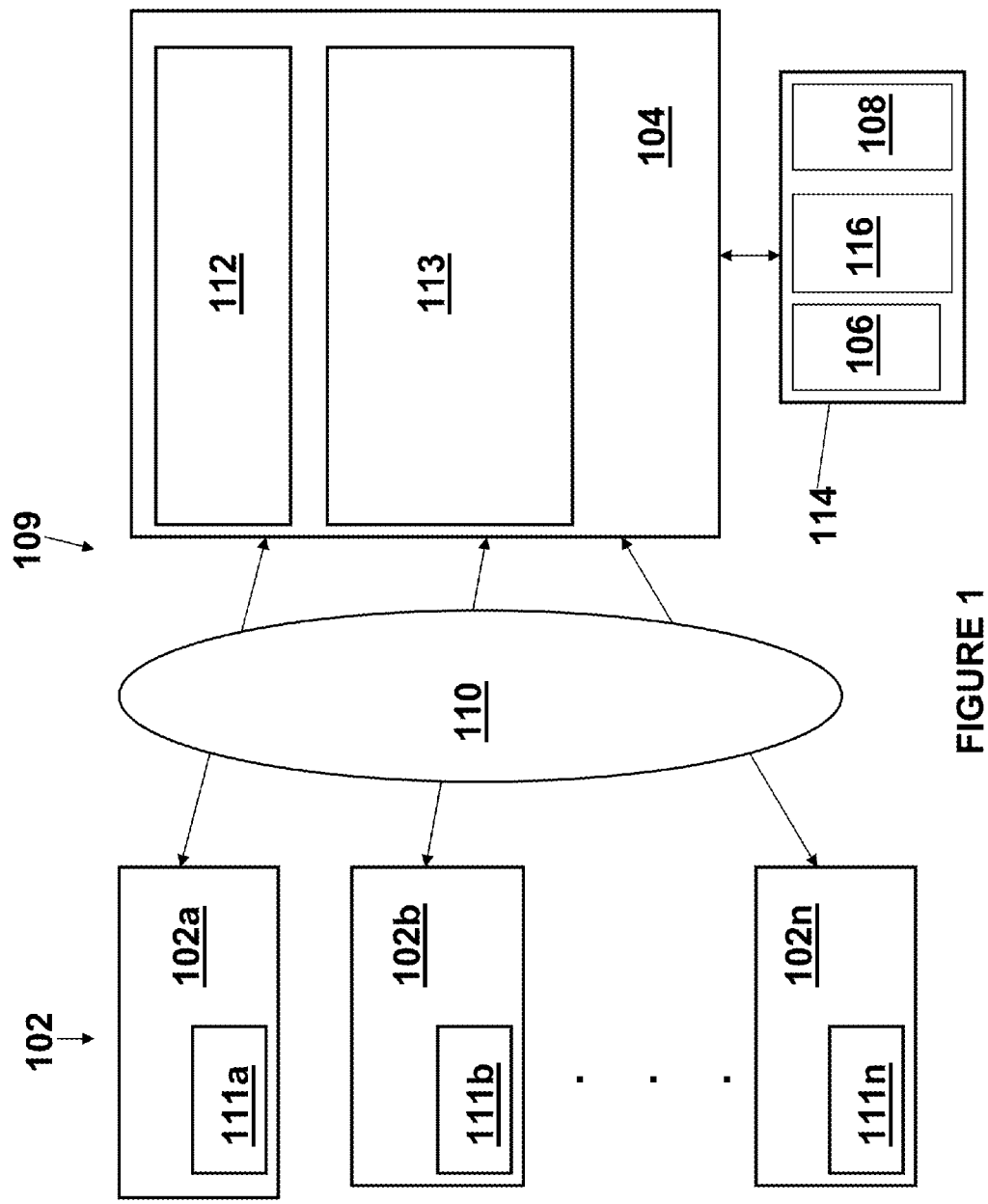
FIG. 1 illustrates an example of a web-based implementation of a physiological imagery generation system.

FIG. 1 illustrates an example of a web-based implementation of a physiological imagery generation system 109 that includes one or more physician units 102, such as physician units 102a, 102b, . . . , 102n, that are capable of establishing a session and communicating with a physiological imagery unit 104 over a link 110. The link 110 may be a wired or wireless link, such as the Internet or World Wide Web, cellular network, digital data network, etc., wherein the physician unit(s) and the physiological imagery unit 104 establish a session and communicate with each other using a known protocol, such as HTTP or HTTPS or other protocols. However, the system is not limited to any particular link as the system may use any communications link, such as a landline or cellular link, or any network link, such as a local area network, wide area network, etc.

Each physician unit 102 may be a processing unit based device that has sufficient processing power, memory and wireless/wired connectivity circuitry to interact with the physiological imagery unit 104. For example, each physician unit 102 may be a personal computer, a terminal, a laptop computer, a mobile device, a pocket PC device, a smartphone (RIM Blackberry, Apple iPhone, etc.), tablet computer, a mobile phone, a mobile email device, etc. Each physician unit 102 may also include an local physiological image unit 111, such as units 111a, 111b, . . . , 111n, that may be, in the exemplary web-based client/server implementation, an physiological imagery application (a plurality of lines of computer code stored in the physician unit and executed by the processing unit of the physician unit) that generates and/or displays physiological imagery (See FIGS. 2-4 for illustrative examples of the physiological imagery) that can be displayed using a typical browser application (not shown) executing on the physician unit wherein the physician receives data/information from the physiological imagery unit 104, such as the physiological imagery to be displayed or the one or more parameters used to generate the physiological imagery.

The physiological imagery unit 104, in one implementation may be implemented as one or more well known server computers (with the typical well known server computer components) that execute one or more pieces of software. In the web-based example shown in FIG. 1, the physiological imagery unit 104 may include a software-based web server 112, such as Apache web servers, executed by the processing unit(s) of the one or more server computer that establish the communications session with each physician unit, generate the web-pages downloaded to each physician unit 102 and receives the data/information from each physician unit. The web server 112 can handle multiple simultaneous communication sessions with a plurality of physician units. The physiological imagery unit 104 may also include a physiological imagery unit 113, implemented as a piece of software executed by the processing unit(s) of the one or more server computer(s) that receives the one or more parameters about a patient and sends that information to each physician unit so that each physician unit can generate the physiological imagery for a particular patient as described below in more detail. Alternatively, the physiological imagery unit 104 that receives the one or more parameters about a patient (such as from an electronic medical record system or any other source) may generate the physiological imagery for the patient based on the one or more parameters and send the generates physiological imagery to the physician unit that requested it as described below in more detail. A characteristic of the physiological imagery may be changed so that the physiological imagery can convey different levels or severity of the physiological condition of the patient as described below in more detail.

The system 109 may further include a data store 114, implemented as one or more databases hosted on one or more database servers in the illustrated implementation (that may be part of the unit 104 or remotely located from the unit 104), that includes a plurality of health records 106 for a plurality of patients (which may also be stored in an electronic medical record system that is remote from the system 109), an physiological image generator rules store 108 that stores that various physiological imagery and rules and the physiological images generated for each physiological condition with the understanding that additional physiological images for additional physiological conditions and additional rules for physiological images may be added into the store 108. The system 109 may also include a user portion 116 that may include various pieces of information about the users of the system. For example, the user portion may have a record associated with each physician/user that uses the system that includes, for example, the preferences for each physician/user of the system.

In addition to the web-based implementation described above, the system may also be implemented as a client/server model, a hosted system model, a standalone computer executing a piece of physiological imagery software (that may be loaded onto a piece of media) or software as a service model in which a physician may send the one or more parameters to the physiological imagery unit 104 that then sends the generated physiological imagery back to the physician unit.

The system 109 may be used to generate physiological imagery in various medical areas. For example, the system 109 may be used to generate physiological imagery to visualize: (1) instantaneous health risk (IHR) according to an organ system, (2) a modifiable health risk (MHR) according to an organ system, (3) a therapeutic analysis of the value of current medications, and (4) an alternative diagnosis probability system. By way of example, an color coded image of an organ might intensify when a combination of lab results appear within a specified time interval. Alternatively, an image might abstract the tolerability of a medication by numerically amalgamating the number and severity of multiple side effects into a single score that can be visualized in a graphical, colorized format. The seminal aspect is therefore consolidation of individual data points into a physiologically interpreted view of the whole.

In operation, the system 109 synthesizes disparate information about a physiological condition in real time into a visual image (the physiological imagery) that is understandable within seconds without the need to read any numbers or text. This interpretive speed does not exist in current electronic medical records and makes the current practice of medicine highly inefficient and riskier due to the time and mental effort required by the physician to create a mental abstraction of the state of the patient. In contrast, the system 109 synthesizes the disparate data about the state of the patient and generates the physiological imagery that visually conveys the state of the patient. Now, several examples of the physiological imagery and the rules to generate the particular physiological imagery are described below. However, the physiological imagery system is not limited to the examples described below nor to the particular states of the patient shown in the examples.

Figure 2:
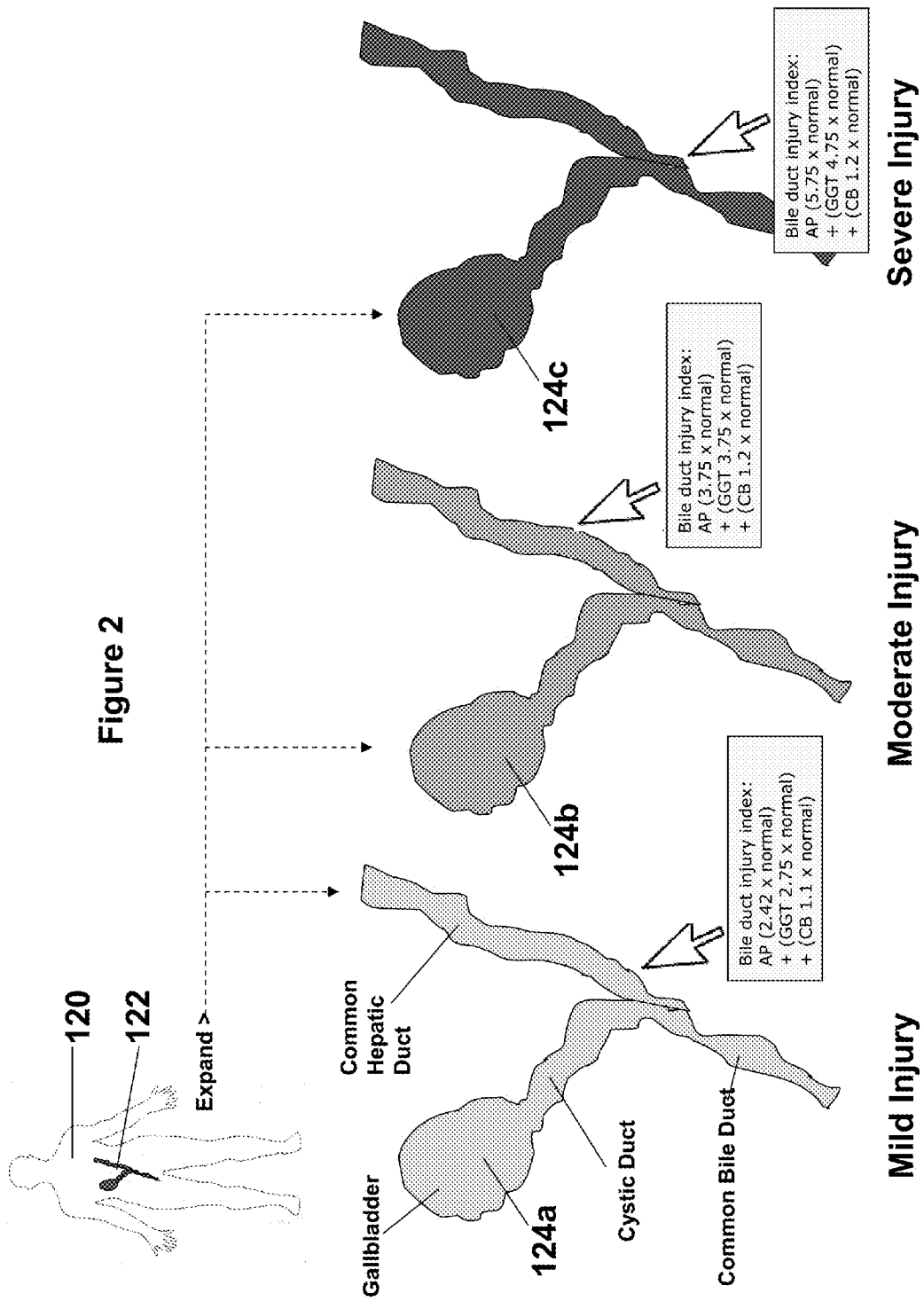
FIG. 2 illustrates a mockup of the physiological image for a new, undiagnosed disease using the physiological imagery system.

FIG. 2 illustrates a mockup of the physiological image for a new, undiagnosed disease using the physiological imagery system. In the example shown in FIG. 2, an organ system image is generated as the physiological image which shows the functional status of any body organ. In FIG. 2, an physiological image 120 is shown which is the human body with an organ system 122 (the bile duct and gallbladder in this example) highlighted so that a physician can visualize the state of the organ wherein the state of the organ is generated based on one or more medical parameters that pertain to the organ. For example, for the gall bladder and bile duct shown in FIG. 2, the combination of simultaneously elevated serum gamma glutanyl transpeptidase (GGT), alkaline phosphatase (AP), and conjugated bilirubin (CB) may suggest inflammation and destruction of the bile duct and gallbladder without damage to the liver itself. The system also allows the user of the system to expand the size of the organ in question.

In the system 109, a characteristic of the physiological imagery may be changed to denote different states of the patient or the organ, etc that allow a user to quickly look at the physiological imagery and determine the state of the patient. The characteristic may be any feature that can be changed to allow someone to visually distinguish between the different states of the patient or the organ, body part, etc. For example, the characteristic may be a color change, a size change, a contrast change, etc. . . . . In one implementation, the characteristic of the physiological image may be the color of the physiological image wherein a first color 124a indicates a first state of the patient (such as mild injury to the organ as shown in FIG. 2), a second color 124b indicates a second state of the patient (such as moderate injury to the organ as shown in FIG. 2) and a third color 124c indicates a third state of the patient (such as severe injury to the organ as shown in FIG. 2). The system 109 is capable of generating a plurality of different states for each physiological image and is not limited to the three states shown in FIG. 2. Thus, in a physiologic image as shown in FIG. 1, this could appear as a red organ (in this case gallbladder and bile ducts) superimposed upon a human figure for quick anatomical identification and with color and intensity proportional to the degree of harm (e.g., lab value patterns and ranges out of the normal expected values).

The system may have one or more sets of rules (stored in the store 108) for each physiological imagery that determines how the characteristic of the physiological imagery is changed to reflect the different states of the patient, body part, organ system, etc. Each rule may use one or more parameters of the patient state or organ system state, such as alkaline phosphatase (AP) for the bile duct and gall bladder, to determine the characteristic of the physiological imagery. For example, for the gallbladder and bile duct organ system shown in FIG. 2, the following rules may be used to determine the characteristic of the physiological imagery:

Light red=(AP 2-3× normal) AND (GGT 2-3× normal) AND (CB<2 times normal) which indicates mild injury of the gallbladder and bile duct organ system;

Medium red=(AP 3-4× normal) AND (GGT 3-4× normal) AND (CB<2 times normal) which indicates moderate injury of the gallbladder and bile duct organ system; and Bright red=(AP>4× normal) AND (GGT>4× normal) AND (CB<2 times normal) which indicates severe injury of the gallbladder and bile duct organ system.

Using the system, a physician can quickly look at the physiological imagery to determine the state of the patient or an organ system of the patient as shown in FIG. 2 wherein the characteristics of the physiological imagery are based on one or more parameters that are associated with the state of the patient or the organ system of the patient. As would be understood, different states of the patient or different organ systems would have different sets of rules that use different parameters and the system and method are not limited to the rules and parameters that appear in the examples set forth herein.

When the physiological imagery is displayed, the physician may click or 'mouse-over' the physiological imagery to see the underlying reasoning, the rules for the physiological imagery and the one or more parameters used to generate the physiological imagery (shown in FIG. 2 for illustration purposes) at any time. Additionally, the implicating lab results may have arrived just a few minutes ago, even during the office visit or during the physical examination itself. Thus, the physiological imagery is updated in real-time (seconds or less) because decisions are made in minutes to seconds in the medical practice.

Figure 3:
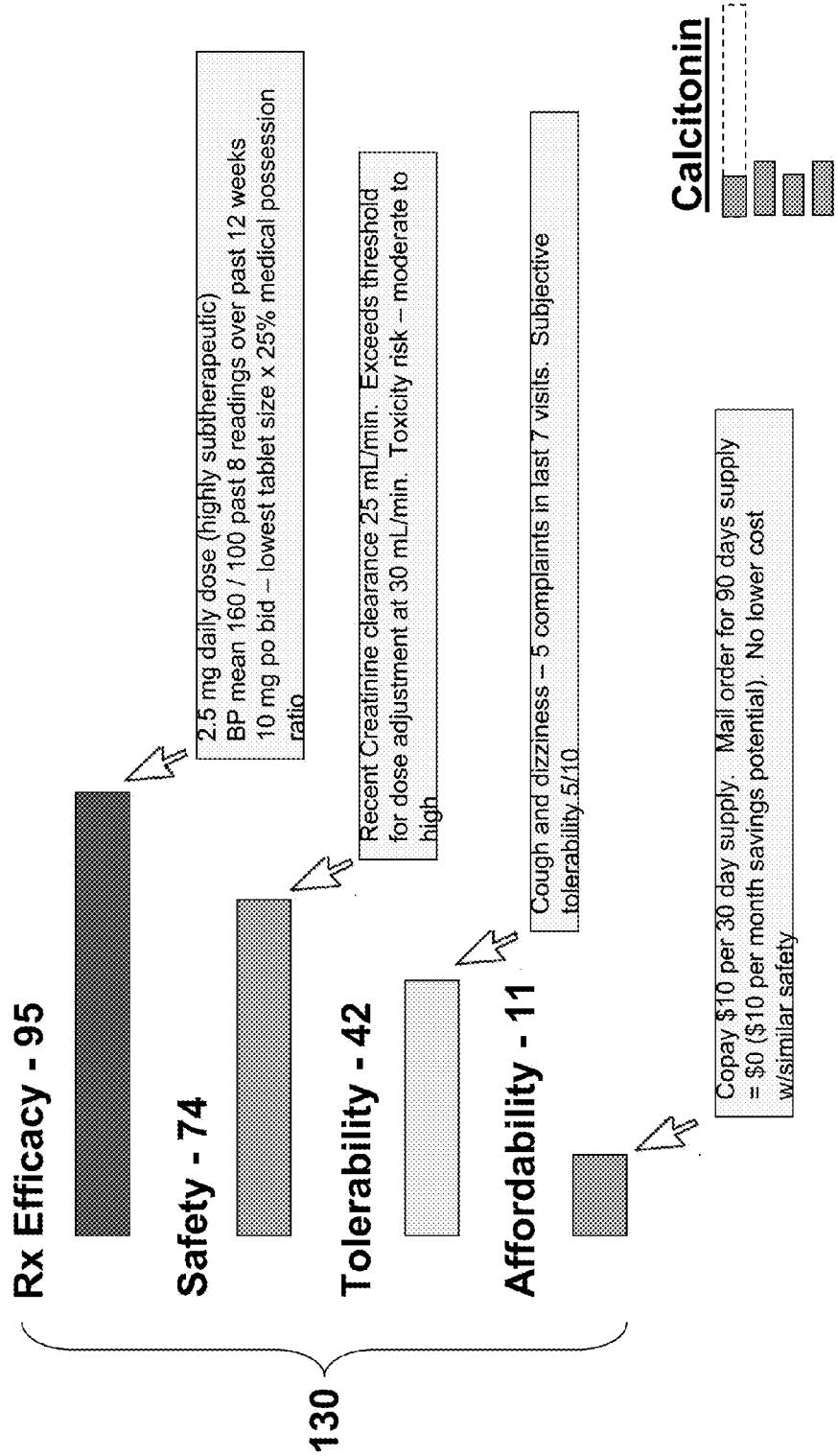
FIG. 3 shows a visual example of an analysis of drug therapy using the physiological imagery system.

FIG. 3 shows a visual example of an analysis of drug therapy using the physiological imagery system. In the example in FIG. 3, the physiological imagery is used to visualize an analysis of drug therapy, in this case lisinopril for hypertension. In this example, the physiological imagery may be one or more indicators 130 (such as one or more bars as shown in FIG. 3) wherein the length of the bar (intended for colorblind doctors) or its color is the changeable characteristic of the physiological imagery that suggests the size of the opportunity to make a relevant action, in this case represented simplistically on a scale of 1 to 100, where 100=most modifiable by some action by the doctor. For example, the drug safety bar, currently appears as a score of 74. This is calculated based on a rule with one or more parameters because the patient's kidney function dropped below a threshold requiring dose adjustment and may have been normal just minutes before the lab result. The patient is close to the threshold, so the bar is not at 100. However, it conveys a continuum of clinical relevance that is readily appreciated. As above, the physician may click or 'mouse-over' the physiological imagery to see the underlying reasoning, the rules for the physiological imagery and the one or more parameters used to generate the physiological imagery (shown in FIG. 3 for illustration purposes) at any time.

Figure 4:
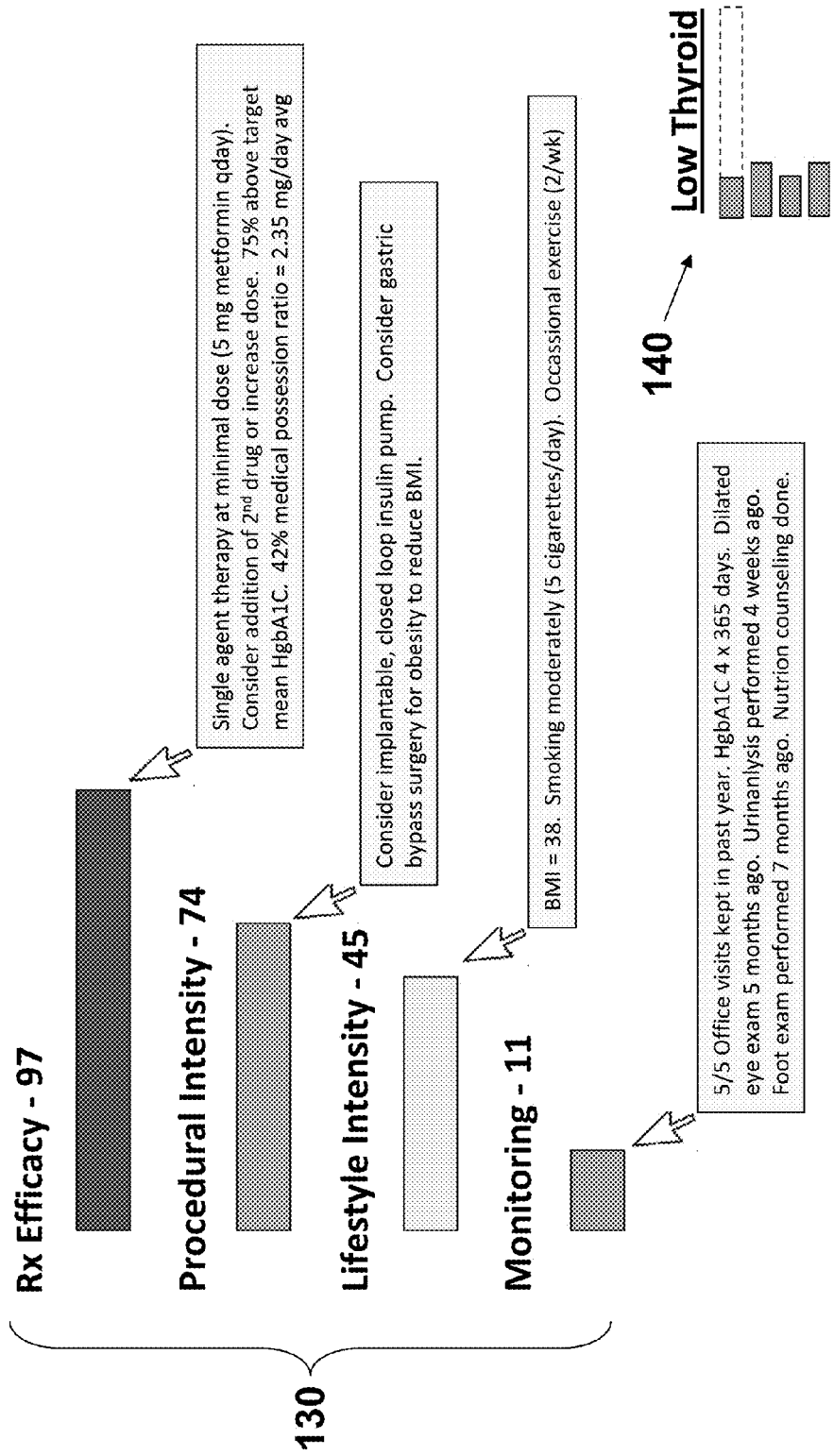
FIG. 4 shows a visual example of a treatment intensity potential for a patient with Type I (insulin-dependent) diabetes mellitus using the physiological imagery system.

As another example of the analysis of drug therapy, if the patient were to suddenly have the arrival of a positive pregnancy test results (a parameter that is received by the system 109), the bar for drug safety would become 100 (long and bright red for example) because lisinopril is very dangerous (teratogenic leading to mutations) for a fetus. As above, the physiological imagery is rendered in real-time for the patient and are most commonly multi-factorial Boolean logic expressions (e.g., A or B and not C within time X) which provide a weighted, interpretive image of the potential to beneficially improve care for the example shown in FIG. 3. In contrast to the lisinopril drug therapy shown, the drug therapy for calcitonin (which is also being taken by the patient) is shown towards to the bottom right in which all of the bars are green and short which means that there is nothing to modify about the calcitonin drug therapy. FIG. 4 shows a visual example of a treatment intensity potential for a patient with Type I (insulin-dependent) diabetes mellitus using the physiological imagery system. In the example shown in FIG. 4, a treatment intensity potential for a patient with Type I (insulin-dependent) diabetes mellitus is shown. In this example, the physiological imagery may be one or more indicators 130 (such as one or more bars as shown in FIG. 4) wherein the length of the bar (intended for colorblind doctors) or its color suggest the size of the opportunity to make a relevant action. As above, the physician may click or 'mouse-over' the physiological imagery to see the underlying reasoning, the rules for the physiological imagery and the one or more parameters used to generate the physiological imagery (shown in FIG. 4 for illustration purposes) at any time.

In the example shown in FIG. 4, there is significant opportunity to increase the patient's medication daily dose (he is taking the lowest possible dose and filling the prescription infrequently) and also for the patient to stop smoking, lose weight, and exercise. As above, the physiological imagery allows the physician to rapidly visualize the patient's status (from an assessment of care to date) rapidly without excessive reading of numbers or text. In contrast, the patient's low thyroid (hypothyroidism) imagery 140 has all small (green) bars, indicating very little potential for therapeutic improvement in care. Using the system, a doctor could thus quickly bypass having to read specific laboratory markers for hypothyroidism or perform a detailed physical exam for the stigmata of hypothyroidism. However, when desired, a simple act such as a 'mouse-over' shows the reasoning behind each of the images' pattern, size, or color which is the interpretation of the underlying data showing why the imagery was generated.

In the above examples, it can be seen that a doctor caring for a patient with multiple co-morbidities and/or taking multiple medications and/or having multiple surgeries can be assessed in a matter of seconds without reading of raw text or numbers. The specifics of the formulas used underneath each imagery rule (e.g., the combination of lab ranges, physical findings, and patterns for bile duct injury in FIG. 2) are not limiting to the system and method since those formula/rules and parameters can be added, deleted or modified at any time and may change with experience and new medical knowledge discovery. In addition, the rules for a particular patient, a particular organ system, a particular drug therapy or a treatment intensity profile (described below) can also modified by each physician or other user of the system.

The categories of interest described above are basic to the practice of medicine. For example, for any disease the broadest scope of possible interventions are (1) medications, (2) procedures including surgery, (3) lifestyle changes, and (4) monitoring (by office visits and/or lab tests). There are no other fundamental treatment categories, so virtually all diseases can be represented using this visually interpretative fashion. In addition, similar universal categories are standards for medication analysis, regardless of location. That is, all medications are intrinsically evaluated by physicians for (1) efficacy, (2) safety, (3) tolerability, and (4) affordability in every case they are used. What has been missing to date is the rapid, real-time synthesis of all pertinent information to distill these analyses down to simple, visualizable abstract images which support and display the underlying physiologic reasoning as to how they were generated, instantly and without physician effort.

In summary, the physiological imagery system and method allows a physician or other medical health care worker to quickly visualize (based on multiple different pieces of medical information/parameters in real-time) a possible new problem with an organ system (an example of which is shown in FIG. 2), an evaluation of the current drugs being taken by a patient (an example of which is shown in FIG. 3) and/or an evaluation of known existing diseases of the patent (an example of which is shown in FIG. 4).

While the foregoing has been with reference to a particular embodiment of the system and method, it will be appreciated by those skilled in the art that changes in this embodiment may be made without departing from the principles and spirit of the system and method, the scope of which is defined by the appended claims.

The invention claimed is:

1. A method for generating physiological imagery of one of a body part and an organ of a patient, the method comprising the steps of:
   receiving one or more parameters about a medical state of one of a body part and an organ of a patient;
   generating physiological imagery of one of a body part and an organ for the patient using an algorithm comprising a multi-factorial Boolean expression that is specific to one of a body part and an organ which is the subject of the imagery based on the one or more parameters by applying the multi-factorial Boolean expression to determine an appearance characteristic of the generated imagery, the physiological imagery being one of an image of a body part and an image of an organ of the patient; and
   changing a display characteristic of the physiological imagery in near real time based on the medical state of the one of a body part and an organ of a patient as indicated by an output of the Boolean expression.

2. The method of claim 1, wherein the characteristic of the physiological imagery is a color of the physiological imagery and wherein generating the physiological imagery of the patient further comprises generating the physiological imagery having one or more different colors based on the state of the patient as indicated by the one or more parameters.

3. The method of claim 1, wherein at least one of the received parameters is selected from a group consisting of: health of an organ or an organ system, health of the patient, a drug therapy analysis and a treatment intensity.

4. The method of claim 1, wherein at least one of the received parameters is selected from a group consisting of: health of an organ or an organ system, wherein the physiological imagery is an image of the organ or organ system and wherein changing the characteristic of the physiological imagery further comprises changing a color of the image of the organ or organ system to indicate a severity of an injury to the organ or organ system.

5. The method of claim 1, wherein the received parameters comprises data representing an analysis of a drug therapy, wherein the physiological imagery is a bar chart of one or more indicators of the result of the analysis of the drug therapy and wherein changing the characteristic of the physiological imagery further comprises changing one of a color and a length of the one or more indicators to indicate an action to be taken by a doctor with respect to the drug therapy.

6. The method of claim 5, wherein the one or more indicators further comprise a drug therapy efficacy indication, a drug safety indication, a drug tolerability indication and a drug affordability indication.

7. The method of claim 1, wherein the received parameters comprises data representing a treatment intensity, wherein the physiological imagery is a bar chart of one or more indicators of the treatment intensity and wherein changing the characteristic of the physiological imagery further comprises changing one of a color and a length of the one or more indicators to indicate an action to be taken by a doctor with respect to the treatment intensity.

8. The method of claim 7, wherein the one or more indicators further comprise a treatment intensity efficacy indication, a treatment procedure intensity indication, a lifestyle intensity indication and a monitoring indication.

9. The method of claim 1 further comprising viewing the one or more parameters about a medical state of a patient associated with the physiological imagery by using a pointing device to point to the physiological imagery.

10. The method of claim 1 further comprising viewing, on a physician unit, the physiological imagery so that a user visualizes the medical state of the patient.

11. The method of claim 10, wherein generating physiological imagery further comprises generating, on the physician unit, the physiological imagery.

12. The method of claim 10, wherein generating physiological imagery further comprises generating, on a physiological imagery unit device remote from the physician unit, the physiological imagery unit device and communicating the physiological imagery over a link to the physician unit.

13. A system for generating a physiological imagery of one of a body part and an organ of a patient, comprising:
   a physiological imagery unit device that receives one or more parameters about a medical state of one of a body part and an organ of a patient; and
   a computer implemented physiological image generator, associated with a computing device, that generates a physiological imagery of one of a body part and an organ for the patient based on medical state of the patient as determined by an algorithm executed by said computer implemented physiological image generator that receives said parameters and comprises a multi-factorial Boolean expression that is specific to one of a body part and an organ which is the subject of the imagery, wherein the physiological imagery is one of an image of a body part and an image of an organ of the patient and wherein the multi-factorial Boolean expression determines a display characteristic of the physiological imagery based on medical state of the patient.

14. The system of claim 13, wherein the characteristic of the physiological imagery comprises one or more different colors based on the medical state of the patient as indicated by the one or more parameters.

15. The system of claim 13, wherein received parameters comprise at least one parameter selected from a list consisting of: health of an organ or an organ system, health of the patient, a drug therapy analysis and a treatment intensity.

16. The system of claim 13, wherein the received parameters comprise a health of an organ or an organ system, wherein the physiological imagery is an image of the organ or organ system and wherein the physiological imagery comprises a color of the image of the organ or organ system to indicate a severity of the injury to the organ or organ system.

17. The system of claim 13, wherein received parameters comprise a drug therapy analysis, wherein the physiological imagery is a bar chart of one or more indicators of the drug therapy analysis and wherein the physiological imagery comprises a color and a length of the bar chart that indicates an action to be taken by a doctor with respect to the drug therapy.

18. The system of claim 17, wherein the one or more indicators represent at least one of: a drug therapy efficacy indication, a drug safety indication, a drug tolerability indication and a drug affordability indication.

19. The system of claim 13, wherein the received parameters comprise a treatment intensity, wherein the physiological imagery is a bar chart of one or more indicators of the treatment intensity and wherein the physiological imagery further comprises a color and a length of the bar chart that indicate an action to be taken by a doctor with respect to the treatment intensity.

20. The system of claim 19, wherein the one or more indicators represent at least one of: a treatment intensity efficacy indication, a treatment procedure intensity indication, a lifestyle intensity indication and a monitoring indication.

21. The system of claim 13 further comprising a physician unit, coupled over a link to the physiological imagery unit device, the physician unit being configured to display the physiological imagery so that a user visualizes the medical state of the patient.

22. The system of claim 21, wherein the physician unit is configured to allow the user to view the one or more parameters about a medical state of a patient associated with the physiological imagery by using a pointing device to point to the physiological imagery.

23. The system claim 21, wherein the physician unit further comprises the computer implemented physiological image generator so that the physiological imagery is generated on the physician unit.

24. The system of claim 21, wherein the physiological imagery unit device further comprises the computer implemented physiological image generator so that the physiological imagery is generated on the physiological imagery unit device and wherein the physiological imagery unit device communicates the physiological imagery to the physician unit.

25. The system claim 21, wherein the physician unit further comprises one of a personal computer, a terminal, a laptop computer, a mobile device, a pocket PC device, a smartphone, a tablet computer, a mobile phone and a mobile email device.

\* \* \* \* \*